(12) United States Patent
Erlbacher et al.

(10) Patent No.: US 7,202,945 B2
(45) Date of Patent: Apr. 10, 2007

(54) DEVICE AND METHOD FOR ANALYZING SAMPLES

(75) Inventors: Andreas Erlbacher, Abtenau (AT); Lutz Niggl, Salzburg (AT); Alois Krutzenbichler, Erlstätt (DE)

(73) Assignee: Tecan Trading AG, Männedorf (CH)

( * ) Notice: Subject to any disclaimer, the term of this patent is extended or adjusted under 35 U.S.C. 154(b) by 276 days.

(21) Appl. No.: 10/878,895

(22) Filed: Jun. 28, 2004

(65) Prior Publication Data

US 2005/0030541 A1 Feb. 10, 2005

(30) Foreign Application Priority Data

Jun. 30, 2003 (CH) .................................. 1148/03

(51) Int. Cl.
*G01N 21/03* (2006.01)

(52) U.S. Cl. .................. 356/246; 402/102; 435/288.4; 436/809

(58) Field of Classification Search ................ 356/440, 356/246; 422/102; 435/288.3, 288.4; 436/809
See application file for complete search history.

(56) References Cited

U.S. PATENT DOCUMENTS

| | | | |
|---|---|---|---|
| 3,849,654 A * | 11/1974 | Malvin | ........................ 356/246 |
| 4,254,223 A | 3/1981 | Schuurs et al. | |
| 4,534,651 A * | 8/1985 | Minikane | ..................... 356/440 |
| 5,355,215 A * | 10/1994 | Schroeder et al. | .......... 356/317 |
| 5,599,503 A | 2/1997 | Man et al. | |
| 6,211,953 B1 * | 4/2001 | Niino et al. | ................. 356/246 |
| 6,410,255 B1 | 6/2002 | Pollok et al. | |
| 6,906,797 B1 * | 6/2005 | Kao et al. | .................... 356/317 |

FOREIGN PATENT DOCUMENTS

| | | |
|---|---|---|
| DE | 3104796 | 9/1982 |
| JP | 63148144 | 6/1988 |
| JP | 9273990 | 10/1997 |
| WO | WO 01/20309 | 3/2001 |

* cited by examiner

*Primary Examiner*—Richard A. Rosenberger
(74) *Attorney, Agent, or Firm*—Notaro & Michalos P.C.

(57) ABSTRACT

The present invention relates to a device (1) and a method for determining parameters of fluid-containing samples (2) in a system (3) for individually irradiating the samples (2) with light (4) of a light source (5) in an essentially vertical irradiation direction (6). In this case, this system (3) includes a detector (7) for measuring the light (8) coming from a single sample, and this detector (7) has a detection direction (9'), which lies on an optical axis (9) that is essentially parallel to the optical axis (6) of the light source (5). This device (1) includes at least one reflective surface (10), using which the light (4) coming essentially vertically out of the light source (5) may be at least partially deflected in an essentially horizontal irradiation direction (11). The device according to the present invention and the method according to the present invention are distinguished in that the detection direction (9') of the detector (7)—for measuring the individual light (8) coming from a single sample (2)—is positioned at an angle to the optical axis of the light (4) irradiating the sample (2) in such a way that only the light (8) coming from the individual sample (2), but not this light (4), reaches the detector (7).

18 Claims, 2 Drawing Sheets

Fig. 3B
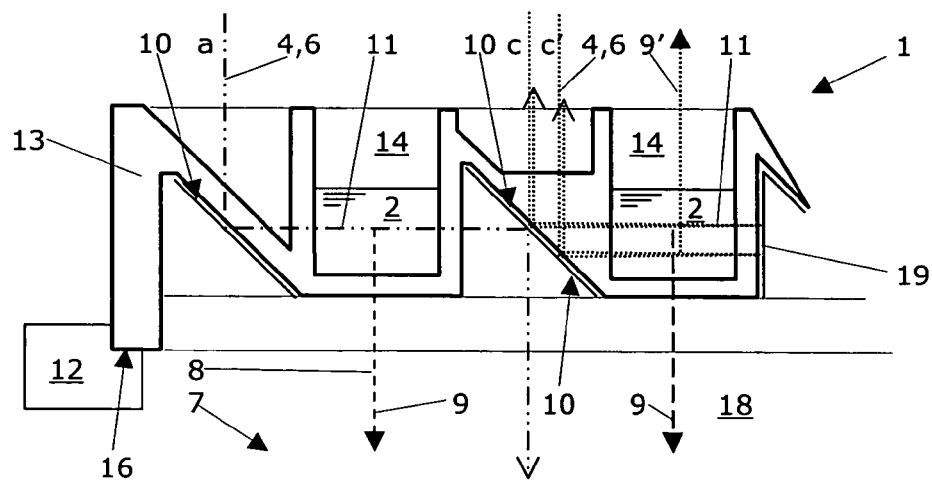
Fig. 4A
Fig. 4B
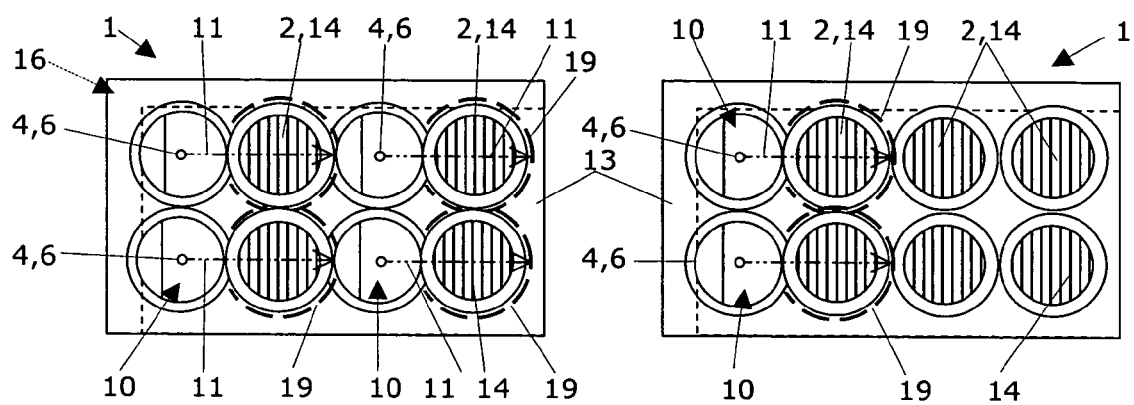
Fig. 4C
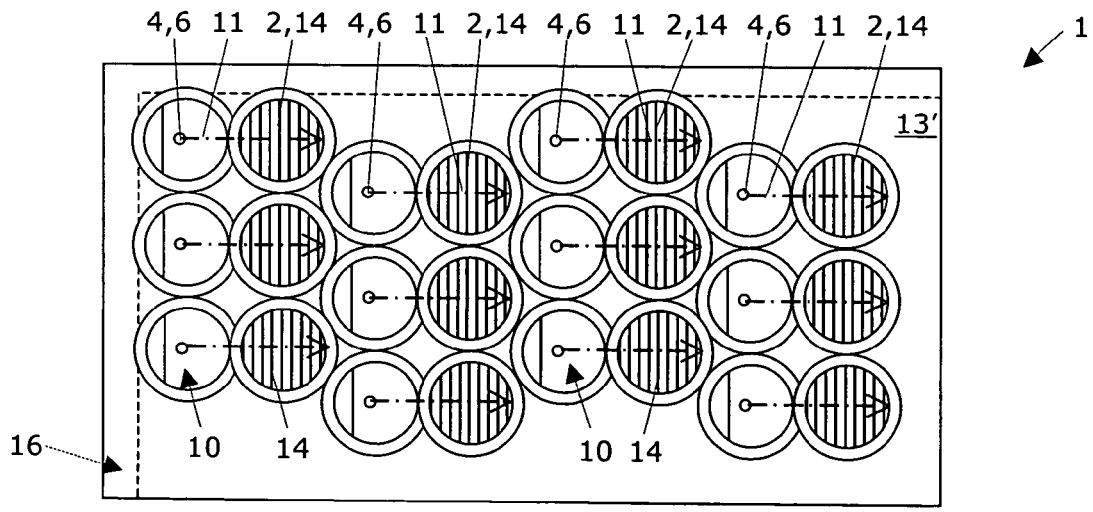

DEVICE AND METHOD FOR ANALYZING SAMPLES

RELATED PATENT APPLICATIONS

This patent application claims priority of the Swiss patent application No. CH 01148/03 filed on Jun. 30, 2003.

FIELD OF THE INVENTION

The present invention relates to a device for use in a system for irradiating fluid-containing samples with light of a light source in an essentially vertical irradiation direction and for determining sample parameters. This system includes a detector for measuring light penetrating a sample and/or triggered in a sample and/or reflected or scattered by a sample. This detector has a detection direction, which lies on optical axis that is essentially parallel to the optical axis of the light source. In this case, such a device includes at least one reflective surface, using which the light coming out of the light source essentially vertically may be at least partially deflected in an essentially horizontal irradiation direction.

DESCRIPTION OF THE PRIOR ART

Such systems are known, for example, as fluorometers for standard microplates and have a similar optical arrangement: the irradiation direction is vertical and the detector is located on the same optical axis. In this way, light penetrating a sample and/or triggered by a sample and/or reflected or scattered by a sample is detected. Devices, which detect the penetrating light, are called photometers; devices, which detect the scattered light, are called nephelometers. Fluorometers only detect the light triggered by the sample. Measurement systems, which combine several of these measurement devices, are called multifunction readers, for example.

Such microplate photometers have the disadvantage that the filling height of the individual wells may be different, so that a different path length of the light beam penetrating the sample results. The filling height is often influenced in this case by the meniscus of the liquid surface in differing ways, which may only be checked with difficulty, so that an individual path length measurement must very often be performed for each individual sample. Such a path length measurement is, however, time-consuming, and in addition two light sources having different wavelengths may be used for this purpose, which makes the device more expensive. Microplates having very many samples, e.g., having 384 or 1536 wells, simplify the automation of the assays of these samples and allow a high processing rate. However, the problems with the different path lengths increase with increasing well count and/or with reduced well content.

Typically, fluorescence is detected in microplates in the reverse direction (180°). Since approximately 5% of the excitation light is reflected by the liquid surface (Fresnel reflection), a large amount of excitation light reaches the detection branch, which results in an increased background signal and finally leads to lower sensitivity in such fluorometers.

Fluorometers into which cuvettes filled with samples are inserted have also been known for some time. Such fluorometers have a different optical arrangement: the irradiation direction is horizontal and at least one detector is located in the same horizontal plane, its optical axis being perpendicular to the optical axis of the light source. Through this angled detector arrangement, only light triggered by a sample and/or reflected or scattered by a sample is detected; no or very little excitation light of this light source reaches the detector directly, which increases the measurement precision. A second detector placed in the same optical axis as the light source may be used for measuring the transmission. The advantage of such fluorometers, which may be referred to in general as "measurement devices based on cuvettes" is that, among other things, due to the cuvette standing upright in the beam path, an exactly reproducible path length of the light beam penetrating the sample is defined. Working with cuvettes is complex, however, and may only be automated with difficulty.

OBJECTS AND SUMMARY OF THE INVENTION

The object of the present invention is to suggest alternative achievements of the object, which retain the advantages of the known fluorometers and/or photometers as much as possible, but eliminate the disadvantages as much as possible.

This object is achieved according to a first aspect in that, a device of the type initially cited is suggested, which is distinguished in that it has at least one reflective surface, using which the light coming essentially vertically out of the light source may be deflected in an essentially horizontal, alternative irradiation direction.

This object is achieved according to a second aspect in that, a corresponding method is suggested, which is distinguished in that, using at least one reflective surface of a device; the light coming essentially vertically out of the light source is deflected in an essentially horizontal irradiation direction.

Preferred embodiments and further features according to the present invention result from the particular dependent claims.

Advantages of the Present Invention Include the Following:

Samples in a microplate, which are irradiated essentially in the horizontal direction, always have equal path lengths.

A microplate reader based on a monochromator may be used and path length measurements may be dispensed with.

High-precision fluorescence measurements may be performed without light, which is incident directly in the sample reaching the detector.

Turbidity and solubility measurements, for which 90° geometry is a requirement, may be performed.

0°, 90°, and 180° fluorometry and 0° absorption, as well as 90° fluorometry, solubility, Raman spectrum, and density measurements may be performed on the same samples.

The sample throughput is very large thanks to microplate technology and all procedures may be automated.

BRIEF DESCRIPTION OF THE DRAWINGS

The present invention will be explained in greater detail in the following on the basis of schematic figures, which represent selected exemplary embodiments and illustrate the present invention, but are not to restrict its scope.

FIG. 3 shows vertical partial sections of variations of a device according to the present invention according to the second embodiment:

FIG. 3B showing a second and third variation;

FIG. 4A shows a top view of a device of the third variation as shown in FIG. 3B;

FIG. 4B shows a top view of a device of a fourth variation of the second embodiment;

FIG. 4C shows a top view of an alternative (offset) arrangement of particular matching reflector and sample wells.

DESCRIPTION OF THE PREFERRED EMBODIMENTS

Figure 1:
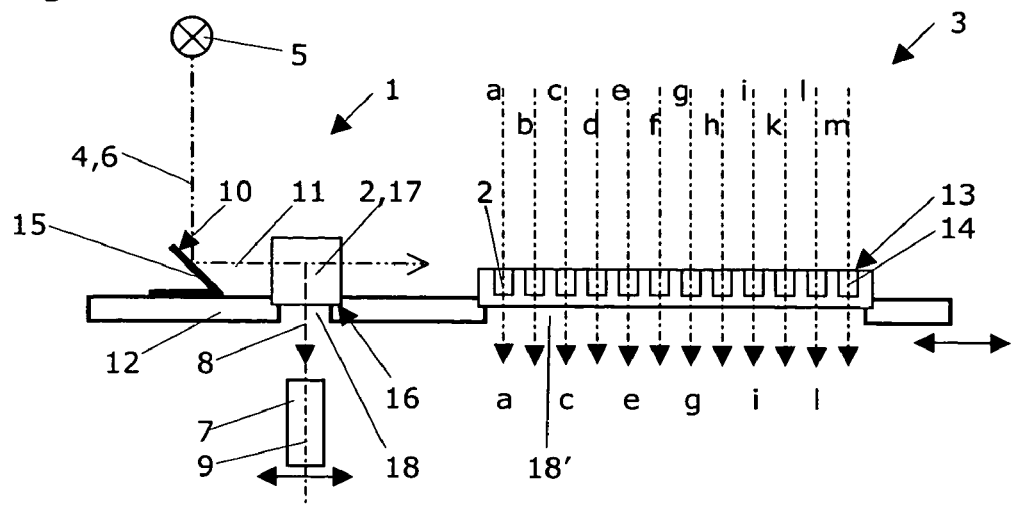
FIG. 1 shows a vertical section through a system for irradiating fluid-containing samples with light of a light source in an essentially vertical irradiation direction and for determining sample parameters, having a device according to the present invention according to a first embodiment.

FIG. 1 shows a device 1 for determining parameters of fluid-containing samples 2 in a system 3 for irradiating the samples 2 with light 4 of a light source 5 in an essentially vertical irradiation direction 6. This system 3 includes a detector 7 for measuring light penetrating a sample and/or triggered in a sample and/or reflected or scattered by a sample. In connection with the present invention, this light triggered in a sample and/or reflected or scattered by a sample is referred to as the "light 8 coming from a sample". This detector 7 lies on optical axis 9, which is essentially parallel to the optical axis 6 of the light source 5.

As an alternative to the embodiment shown, one end of an optical fiber may be seated at the location of the detector 7 shown in FIG. 1, and this optical fiber may guide the light 8 coming from the sample to the actual detector. It is important in any case that the effective detection direction 9, 9' lies parallel to the optical axis 6; this may be achieved by using an optical fiber whose optical input is positioned in the desired detection direction and whose optical output discharges into the detector, for example. Such a detector may be positioned in practically any arbitrary direction and anywhere in a system 3 for determining parameters of fluid-containing samples 2.

In a first embodiment, this device 1 according to the present invention includes a single reflective surface 10 here, using which the light 4 coming essentially vertically out of the light source 5 may be deflected in an essentially horizontal irradiation direction 11. This light 4 irradiates a horizontally laid standard cuvette 17 containing a sample 2, whose opening was sealed. Water-repellent, elastic films, such as Parafilm® (Pechiney Plastic Packaging, Inc.) or stoppers are suitable for the sealing. A plastic cuvette or a glass cuvette and/or quartz glass cuvette 17, which has a reduced height and is placed standing vertically over a first opening 18, may also be used. Light triggered by the sample 2 in the cuvette 17 and/or reflected or scattered by the sample, i.e., light 8 coming from the sample, reaches the detector 7 through the opening 18 provided for this purpose in the movable carrier 12. The incident light is measured there and the measurement signals are then relayed to a digital computer unit (not shown) to be analyzed and displayed and/or stored.

Simultaneously, a standard microplate 13 having wells 14 may be placed on the carrier 12 of the system 3 in such a way that it lies over a second opening 18'. The samples 2 in a row of wells a-m may then be assayed using vertical irradiation. A double arrow shown under the detector 7 indicates that the detector may be movable. The detector may—if desired—be displaced enough that its optical axis 9 is coincident with the optical axis 6 of the light source 5. In this detector position, the 0° fluorometry or 0° absorption of the samples may be measured using the same detector 7 as previously for the 90° fluorometry, the solubility measurement, the recording of a Raman spectrum, and/or the density measurements performed on the cuvette 17. As an alternative to the mobility of the detector 7, the light source 5 or both elements may be movable. A second detector (not shown) may also be provided, which has precisely the necessary distance to the first detector 7.

In any case, it is preferable for the carrier 12 to be movable like a mechanical stage in the X and Y directions. One or more cuvettes 17 and/or one or more microplates 13 may be placed on the carrier 12 in the region of corresponding openings 18, 18'. For example, a stock solution or another reference liquid for the samples 2 to be assayed in the microplate 13 may be poured into such a cuvette 17.

The first embodiment of the device 1 according to the present invention for use in a system 3, which includes an essentially horizontal carrier 12, movable in the X and/or Y directions, for microplates 13 having wells 14, is distinguished in that it is implemented as this carrier 12. For this purpose, the device 1 includes at least one mirror 15 having a reflective surface 10 and a support surface 16 assigned to the mirror 15 for placing a cuvette 17 containing a sample 2. In addition, this device 1 includes an opening 18 in the region of the support surface 16 for letting through light triggered in the sample and/or reflected or scattered by the sample, i.e., light 8 coming from the sample, to the detector 7. This mirror 15 is preferably a glass mirror coated with aluminum. The mirror 15 may also, however, include a reflective surface 10 made of plastic or may be manufactured entirely from plastic. Suitable plastics partially reflect the excitation light (approximately 5%) and therefore do not necessarily have to be coated. For measuring the light 4 transmitted through the sample 2, a second mirror (not shown) may be positioned behind the cuvette 17, which deflects this transmitted light 4 to an additional detector (not shown) positioned above the sample plane.

Figure 2:
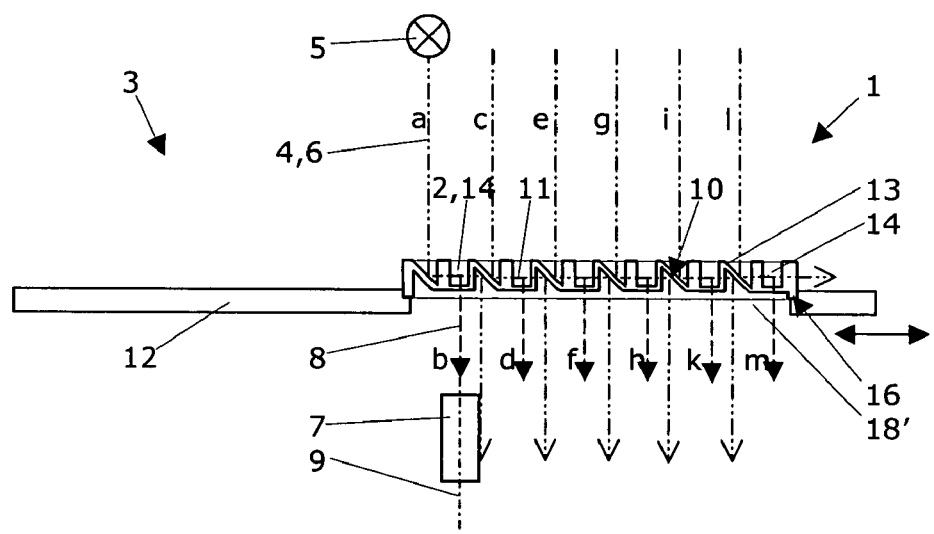
FIG. 2 shows a system as shown in FIG. 1, having a device according to the present invention according to a second embodiment.

According to a second embodiment, the device 1 according to the present invention for use in a system 3, which includes an essentially horizontal carrier 12, which is movable in the X and/or Y directions, for microplates 13 having wells 14, is distinguished in that the device 1 is implemented as one of these microplates 13. This is shown in FIG. 2, where a microplate 13 according to the present invention is placed on the carrier 12 of the system 3 in such a way that it lies over a second opening 18'. The wells a, c, e, g, i, l in a row are irradiated one after another with light 4 from the light source 5. There, the light beams are each deflected on a reflective surface 10 in the alternative, horizontal irradiation direction 11 and traverse the neighboring wells b, d, f, h, k, m, in each of which a sample 2 is located. Particularly in the especially preferred embodiment shown in FIG. 3B (see well c there), a reflective coating of the reflective surface 10 may be dispensed with, because the plastic-air transition (45° surface) acts as a totally-reflecting mirror for the light coming from above or from the right even without a coating.

By displacing the carrier 12, the wells b, d, f, h, k, m having the irradiated samples 2 are positioned over the detector 7 one after another in such a way that the light triggered in the sample and/or reflected or scattered by the sample, i.e., the light 8 coming from the sample, reaches the detector 7 and may be measured by it.

By displacing the light source 5 and/or the detector 7 or by using a second detector or a second light source, the optical axis 9 of the detector 7 may be made to coincide with the optical axis 6 of the light source 5, and therefore a 0° measurement of the light 4 transmitted through the samples may also be performed in each of the wells b, d, f, h, k and m.

According to a first variation of the second embodiment (cf. FIG. 3A), the device, which is conceived as a microplate, includes multiple reflective surfaces 10 and wells 14, each well 14 being assigned a reflective surface 10 (cf. FIGS. 4A and 4C). For example, a microplate 13, 13' includes an equal number of wells 14 as reflective surfaces 10, i.e., each sample 2 may be irradiated horizontally and vertically.

However, a device 1 may also be provided which includes multiple reflective surfaces 10, each of which is assigned to a well 14 (cf. FIG. 4B). For example, a microplate 13 includes only one reflective surface 10 per row of wells 14, i.e., in a microplate having 96 wells (8×12), only one sample 2 per row may be irradiated horizontally and vertically. A microplate 13 may also only have one single reflective surface 10 (not shown), so that the reference sample may be placed not in a cuvette 17 (cf. first embodiment shown in FIG. 1), but rather in a well 14 of a microplate 13.

Figure 3A:
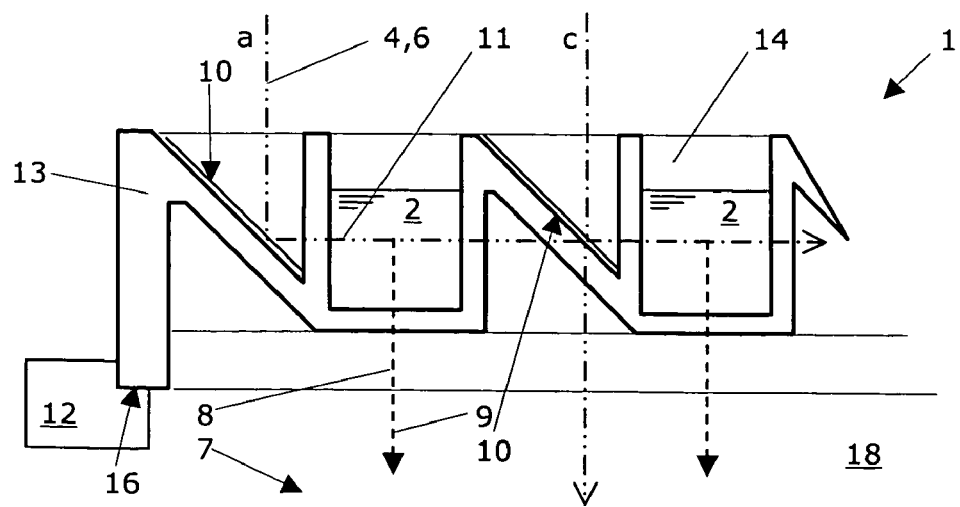
FIG. 3A showing a first variation.

FIG. 3A shows a vertical partial section of a first variation of a device according to the present invention according to the second embodiment. It is obvious that the light 4 from the light source 5 penetrates the wells a and c of the microplate 13 in the direction of the essentially vertical optical axis 6. In well a, the light beam is incident on a reflective surface 10 and is deflected by this surface in an essentially horizontal direction 11. The light beam then penetrates a first wall of the well 14, the sample 2, and a second wall of the well. In order that the light beam may be reflected better on the oblique plane, which the reflective surface 10 represents, this oblique plane is preferably thinly coated with aluminum. This coating may be applied, for example, in a PVD process (physical vapor deposition) or even in a CVD process (chemical vapor deposition). Because the same applies for well c as for well a, this oblique plane preferably also has such a metal coating for the reflective surface 10. Therefore, a part of the upper surface of the microplate 13 is preferably metal-coated and each well 14, which contains a sample, is assigned a reflective surface 10. Providing such a coating has the advantage that only the intended well 14 having the sample 2 contained therein, which is located directly next to the well having the reflective surface 10 impinged by the light beam 4, 6, is penetrated by this light beam. The reflective surfaces 10 of the wells following in the illumination direction prevent the light beam from illuminating a second sample. As is also obvious from FIG. 3A, the liquid level of the samples 2 in the wells 14 plays a subordinate role; the path length of the light beam penetrating the sample is constant. The only requirement is that the light beam runs below the liquid surface. The part of the light which passes the sample is deflected downward at the following reflective surface 10 and may thus be relayed to a second detector (not shown), while the part of the light triggered by the sample and/or reflected or scattered by the sample is incident on the detector 7 through the floor of the well 14 and is measured by the detector.

FIG. 3B shows a vertical partial section of a second and third variation of a device according to the present invention according to the second embodiment. It is obvious that the light 4 from the light source 5 penetrates the wells a and c of the microplate 13 in the direction of the essentially vertical optical axis 6. In well a, the light beam is incident on a reflective surface 10 and is deflected by this surface in an essentially horizontal direction 11. The light beam then penetrates a first wall of the well 14, the sample 2, and a second wall of the well. In order that the light beam may be reflected better on the oblique plane, which the reflective surface 10 represents, this oblique plane is preferably thinly coated with aluminum. This coating may be applied, for example, in a PVD process (physical vapor deposition) or even in a CVD process (chemical vapor deposition). Because the same applies for well c as for well a, this oblique plane preferably also has such a metal coating for the reflective surface 10. Therefore, a part of the lower surface of the microplate 13 is preferably metal coated and each well 14, which contains a sample, is assigned a reflective surface 10. Providing such a coating has the advantage that only the intended well 14 having the sample 2 contained therein, which is located directly next to the well having the reflective surface 10 impinged by the light beam 4, 6, is penetrated by this light beam. The reflective surfaces 10 of the wells following in the illumination direction prevent the light beam from illuminating a second sample. As is also obvious from FIG. 3B, the liquid level of the samples 2 in the wells 14 plays a subordinate role; the path length of the light beam penetrating the sample is constant. The only requirement is that the light beam runs below the liquid surface. The part of the light which passes the sample is deflected downward at the following reflective surface 10 and may thus be relayed to a second detector (not shown), while the part of the light triggered by the sample and/or reflected or scattered by the sample is incident on the detector 7 through the floor of the well 14 and is measured by the detector.

Well c differs from well a in that it is partially filled with microplate material, e.g., plastic, glass, or quartz glass. This allows the number of phase transitions, which the light beam must pass through to be reduced. Well d differs from well b in that it has a mirrored wall 19, which reflects the light penetrating the well back in the direction of the light source. A further detector may therefore also be positioned directly next to the excitation light source 5. This detector is then used, for example, for detecting the 180° fluorescence or 90° fluorescence from above in the direction 9' (cf. FIG. 3B, wells c and d). The variation according to the wells c and d in FIG. 3B has the further advantage that the excitation light 4 traverses the well 14 twice, through which a higher signal yield may be achieved. This is true in any case, no matter if the measurement is performed from above with a detector in the optical axis 9' or from below with a detector in the optical axis 9.

The top view in FIG. 4A shows a microplate 13 having further well pairs which correspond to the wells c and d in FIG. 3B. The top view in FIG. 4B shows a microplate 13 which has only one single well pair which corresponds to the wells c and d in FIG. 3B per row of wells. A reflective surface 10 and a wall 19 on the side facing away from the reflective surface 10 are assigned to all of these wells d. This wall 19 is preferably implemented as mirrored and/or opaque to light. This reflective surface 10 is also preferably made of an aluminum coating here. However, such a metal coating may be dispensed with because the plastic of the microplate partially (approximately 5%) reflects the excitation light. An alternative (offset) arrangement of the particular associated reflector wells a and/or c etc. and sample wells b and/or d etc. is advantageous in such cases. Thus, for example, a light beam penetrating a sample well b and/or d etc. is not incident on a further reflector well c and/ore and a sample well d and/or f lying behind it, but rather only on the intermediate walls of the neighboring well (cf. FIG. 4C). Time-saving scanning of the alternative microplate 13' is also possible, because the sample wells are positioned in a straight row next one another.

Any arbitrary combinations of the features of the embodiment shown are described are possible in the scope of the present invention. The reference numbers in the figures identify identical elements, even when this is not expressly noted in the text.

What is claimed is:

1. A device for determining parameters of fluid-containing samples, the device being implemented to be introduced into a system for individually irradiating the samples with light of a light source, which emits light in a direction of an optical axis of the light source that extends in a substantially vertical direction, the system including a detector for measuring the light coming from a single sample, and the detector having a detection direction that lies on an optical axis, which is substantially parallel to the optical axis of the light source, the device at least one reflective surface implemented to deflect the light of the light source into a substantially horizontal irradiation direction for irradiating the sample, wherein the detection direction of the detector being positioned offset to the optical axis of the light source in such a way that only the light coming from the individual sample, but not the light emitted by the light source or deflected by the reflective surface, reaches the detector, and wherein the system includes a substantially horizontal carrier with an opening for microplates, and wherein the device is implemented as one of the microplates.

2. The device according to claim 1, wherein the angle between the detection direction of the detector and the optical axis of the light irradiating the sample is 90°.

3. The device according to claim 1, wherein the carrier is movable in at least one of the X or Y directions.

4. A device for determining parameters of a fluid-containing sample, the device being implemented to be introduced into in a system for individually irradiating samples with light of a light source, which emits light in direction of an optical axis that extends in an essentially vertical direction, this system including a detector for measuring the light coming from a single sample, and this detector having a detection direction that lies on an optical axis, which is essentially parallel to the optical axis of the light source, and the device including at least one reflective surface implemented to deflect the light of the light source into an essentially horizontal irradiation direction for irradiating the sample, wherein the detection direction of the detector is positioned offset to the optical axis of the light source in such a way that only the light coming from the individual sample, but not the light emitted by the light source or deflected by the reflective surface, roaches the detector, wherein the system includes an essentially horizontal carrier with an opening for microplates, and wherein the device has the dimensions of a standard microplate and includes a mirror having the reflective surface and a support surface assigned to the mirror for placing a cuvette containing a sample, the device including an opening in the region of the support surface for passage of light triggered in the sample or reflected by the sample to the detector.

5. The device according to claim 4, wherein the carrier movable in at least one of the X or Y directions, and wherein the angle between the detection direction of the detector and the optical axis of the light irradiating the sample is 90°.

6. The device according to claim 1, which includes multiple reflective surfaces and wells, a reflective surface being assigned to each well.

7. The device according to claim 6, wherein a wall on the side facing away from the reflective surface is assigned to those wells of the device to which a reflective surface is assigned.

8. The device according to claim 7, wherein the wall on the side facing away from the reflective surface is implemented as mirrored or opaque to light.

9. The device according to claim 6, comprising a upper and lower surface, at least one of its the upper surface or lower surface is at least partially mirrored.

10. A system for determining parameters of fluid-containing samples, the essentially horizontal carrier of is movable in at least one of the X or Y directions, wherein the system includes at least one device according to one of claims 1 or 4.

11. A method for determining parameters of fluid-containing samples in a system for individually irradiating samples with light of a light source, the method comprising the following steps:
a) introducing into this system a device according to claim 1 or 4 for determining parameters of fluid-containing samples;
b) emitting light with the light source of the system in direction of optical axis that extends in an essentially vertical direction;
c) deflecting at least a part the light of the light source into an essentially horizontal irradiation direction and irradiating a sample with this deflected light;
d) measuring the light coming from a single, irradiated sample with a detector that lies on an optical axis, which is essentially parallel to the optical axis of the light source, wherein the individual light coming from a single sample is measured in a detection direction, which is positioned offset to the optical axis of the light source in such a way that only the light coming from the single sample reaches the detector, but not the light that is emitted by the light source or is deflected by the reflective surface.

12. The method according to claim 11, wherein the angle between the detection direction of the detector and the optical axis of the light irradiating the sample is 90°.

13. The method according to claim 11, which is applied for analyzing fluid-containing samples.

14. The method according to claim 11, system in which multiple samples are filled into multiple wells of a microplate and each sample is analyzed individually, wherein all process steps are automated.

15. The method according to claim 11, in which at least one sample is filled into at least one cuvette and each sample in the at least one or more cuvettes is analyzed individually.

16. The method according to claim 11, in which the samples are analyzed in wells of a microplate.

17. The method according to claim 11, in which a sample is analyzed in a cuvette.

18. The method according to claim 11, in which the samples are analyzed in wells of a microplate, wherein parameters of at least one fluid-containing sample are determined in a cuvette.

* * * * *